United States Patent
Chen et al.

(10) Patent No.: US 10,575,871 B2
(45) Date of Patent: Mar. 3, 2020

(54) FULLY DETACHABLE TROCAR

(71) Applicant: UNIMICRO MEDICAL SYSTEMS (SHENZHEN) CO., LTD., Shenzhen, Guangdong (CN)

(72) Inventors: Weichung Chen, Guangdong (CN); Xinfeng Chen, Guangdong (CN)

(73) Assignee: UNIMICRO MEDICAL SYSTEMS (SHENZHEN) CO., LTD. (CN)

(*) Notice: Subject to any disclaimer, the term of this patent is extended or adjusted under 35 U.S.C. 154(b) by 325 days.

(21) Appl. No.: 15/752,567

(22) PCT Filed: Apr. 13, 2015

(86) PCT No.: PCT/CN2015/076390
§ 371 (c)(1),
(2) Date: Feb. 13, 2018

(87) PCT Pub. No.: WO2016/119310
PCT Pub. Date: Aug. 4, 2016

(65) Prior Publication Data
US 2018/0214177 A1    Aug. 2, 2018

(30) Foreign Application Priority Data
Jan. 28, 2015 (CN) .......................... 2015 1 0044254

(51) Int. Cl.
*A61B 17/34* (2006.01)
*A61B 17/02* (2006.01)

(52) U.S. Cl.
CPC ...... *A61B 17/3423* (2013.01); *A61B 17/0218* (2013.01); *A61B 17/3474* (2013.01);
(Continued)

(58) Field of Classification Search
CPC . A61B 17/3423; A61B 17/34; A61B 17/0218; A61B 17/3498; A61B 2017/3419; A61B 2017/3482
See application file for complete search history.

(56) References Cited

U.S. PATENT DOCUMENTS 5,454,791 A * 10/1995 Tovey ................ A61B 17/3494
                                                    604/118
8,157,833 B2 * 4/2012 Au ........................ A61B 17/34
                                                    606/105
(Continued)

OTHER PUBLICATIONS

International Search Report dated Oct. 21, 2015, in PCT/CN2015/076390 (with English translation) (6 pages).
(Continued)

*Primary Examiner* — Ellen C Hammond

(57) ABSTRACT

Disclosed is a fully detachable trocar, comprising: a cannula; a support connected to one end of the cannula; a channel passing through the cannula and the support along an axial direction; an air-inflated structure arranged on the support and communicated with the channel; an air valve for controlling the air-inflated structure to turn on and off; a primary sealing component for sealing when a device is used; and a second sealing component for sealing when no device is used; the primary sealing component, the second sealing component and the support are connected in a sealing manner from top to bottom in sequence, and the primary sealing component can be independently separated from the second sealing component which can be independently separated from the support, so as to provide multiple methods for taking out tissues.

8 Claims, 11 Drawing Sheets

(52) U.S. Cl.
CPC .. *A61B 17/3498* (2013.01); *A61B 2017/3407* (2013.01); *A61B 2017/349* (2013.01); *A61B 2017/3419* (2013.01); *A61B 2017/3486* (2013.01)

(56) References Cited

U.S. PATENT DOCUMENTS

2010/0274193 A1* 10/2010 Patton ................ A61B 17/3462
604/167.01
2013/0030372 A1* 1/2013 Franer ................ A61B 17/3439
604/164.11

OTHER PUBLICATIONS

Written Opinion dated Oct. 21, 2015, in PCT/CN2015/076390 (with English translation) (11 pages).
International Preliminary Report on Patentability dated Aug. 1, 2017 in PCT/CN2015/076390 (with English translation) (13 pages).

* cited by examiner

FULLY DETACHABLE TROCAR

CROSS-REFERENCE TO RELATED APPLICATIONS

The present invention is filed under 35 U.S.C. § 371 as the U.S. national phase of International Patent Application No. PCT/CN2015/076390, filed Apr. 13, 2015, which designated the U.S. and claims the benefit of priority to Chinese Patent Application No. 201510044254.8, filed Jan. 28, 2015, each of which is hereby incorporated in its entirety including all tables, figures and claims.

TECHNICAL FIELD

The present invention relates to the field of medical devices, and more particularly, to a trocar.

BACKGROUND

A trocar is a common tool in a laparoscopic surgery. An inflating needle is penetrated into an umbilical region of a patient during surgery. Meanwhile, the air is injected into the enterocoelia to expand the enterocoelia space, and then the trocar is penetrated into the enterocoelia to form a channel to facilitate the operation of the surgery. It is obvious for the importance of air impermeability in this process. In order to guarantee that the air in the stomach of a patient in the surgery process will not be leaked out, the existing trocar is provided with a sealing structure including sealing plates for sealing when there is a surgical device and a non-return part used when no surgical device is used. The trocar in the prior art has the following defects:

1. Both the sealing plates and the non-return part are provided with an opening. The sizes of the openings are also inconsistent since the functions thereof are different. Generally, in order to better cover the surgical device, the opening of the sealing plate shall be smaller than the opening of the non-return part. However the sealing plates cannot be independently detachable from the non-return part since they are integrated with each other. When a bigger tissue needs to be taken out, although the tissue can be taken out if the sealing structure is removed, air leakage may be caused; and although the tissue can pass through the non-return part if the sealing structure is remained, the tissue will be clamped by the sealing plates, and can be taken out only after being segmented in the enterocoelia, which seriously affects the surgery efficiency and increases the operation difficulty.

2. The opening of the sealing plate is of a type of round hole, which has a higher resistance against insertion and pulling; moreover, the recovery speed is lower after the surgical device is pulled out from the round hole, and air leakage is easily caused when a smaller surgical device is inserted.

3. The external wall of a cannula only has an unilaterally arranged barb, and the device has the risk of bringing the cannula to divorce from a human body when pulling out.

4. The puncturing tool in the prior art is easy to break in use since a visual plastic tool bit is adhered to a stainless toolbar.

SUMMARY

In order to overcome the deficiency of the prior art, the present invention provides an fully detachable trocar, with the following advantages: providing multiple methods for taking out samples, and being applicable to most surgery occasions; effectively preventing air leakage by providing multiple sealing structures; quick discharge, which saves the surgery time; and better fixing the trocar, thus preventing the trocar from loosening in surgery, which is convenient for medical workers to operate.

The technical solution adopted by the present invention to solve the technical problems is as follows.

A fully detachable trocar comprising:
a cannula;
a support connected to one end of the cannula;
a channel passing through the cannula and the support along an axial direction for guiding an device;
an air-inflated structure arranged on the support and communicated with the channel;
an air valve for controlling the air-inflated structure to turn on and off;
a primary sealing component for sealing when an device is used; and
a second sealing component for sealing when no device is used;
wherein the primary sealing component, the second sealing component and the support are connected in a sealing manner from top to bottom in sequence, and the primary sealing component can be independently separated from the second sealing component which can be independently separated from the support, so as to provide multiple methods for taking out tissues which is distinguished from the single opening method in the prior art, As a further improvement to the solution above, the primary sealing component comprises:
a primary sealing seat with an axial through hole;
a primary sealing membrane fixedly connected at an external edge thereof to the through hole and provided at a center thereof with a round hole, wherein the device can be encircled by the primary sealing membrane when passing through the round hole to form an airtight structure, and a close-fitting with the device can be maintained by the primary sealing membrane as the device moves;
a plurality of sealing plates uniformly arranged along a periphery of the round hole, with one end being fixedly connected to the primary sealing membrane and the other end extending to a central region of the round hole, wherein neighboring sealing plates are partially overlapped to form a lens-type leaf structure; when the device passes through the round hole, the sealing plates are fit with a periphery of the device to form an airtight structure, and can recover to an initial status quickly after the device is pulled out, so as to adapt to the sealing requirements of devices with different sizes; and the sealing plates are arranged at either side of the round hole to enable the device to keep sealing in the process of inserting in and pulling out.

As a further improvement to the solution above, the primary sealing component comprises a plurality of guide plates, the guide plates collectively form a via hole coaxial with the round hole for guiding the device so that the device can only pass through the round hole, which prevents the device from deviation to puncture the primary sealing membrane to cause air leakage; and the guide plates are arranged at either side of the primary sealing membrane.

As a further improvement to the solution above, the second sealing component comprises:
a shell;

a second sealing seat arranged within and connected to the shell in a sealing manner, the second sealing seat is provided with an axial through hole; and a second sealing membrane fixedly connected at an outer edge thereof to the through hole and provided at a center thereof with a finedraw, so that the first sealing membrane can be naturally closed to form an airtight structure when no instrument is used, and normal insertion of the device cannot be hindered either.

As a further improvement to the solution above, the second sealing seat is provided with a sealing structure for sealing with the shell, and the second sealing membrane and the sealing structure are mutually separated, so that the second sealing membrane cannot be deformed due to the sealing connection between the second sealing seat and the shell;

the second sealing seat is fixedly connected to the shell, so as to limit the movement thereof relative to the shell, and avoid the sealing structure from deformation under a friction force;

the second sealing membrane comprises a plane provided with the finedraw, and cambered surfaces arranged at either side of the plane; and each of the camber surfaces is provided with a reinforcing rib perpendicular to the finedraw, which enables the finedraw to be recovered quickly after the instrument is pulled out, so as to avoid air leakage.

As a further improvement to the solution above, the cannula comprises:

a plurality of first barbs uniformly arranged at an outer surface of the cannula; and a plurality of reversed second barbs arranged among the first barbs and spaced apart a certain distance from one another;

the first barbs and the second barbs are used for fixing the catheter in two directions, and preventing the instrument when pulled out from driving the catheter to divorce from a human body.

As a further improvement to the solution above, the cannula has an end with an indication structure to facilitate displaying a position of the cannula.

As a further improvement to the solution above, the support is provided with an annular kinking structure, which can fix the cannula into skin through suture.

As a further improvement to the solution above, the air-inflated structure is clamped in the support and is sealed by glue. Compared with the single gluing form, the fixation strength of the air-inflated structure can be increased, so as to prevent air leakage phenomenon caused by collision and other external force damages.

As a further improvement to the solution above, further comprising a puncturing tool including: a toolbar with a colored catheter sleeve for facilitating the medical workers to observe whether the toolbar penetrates through an abdominal wall; and a tool bit integratedly connected to the toolbar.

The beneficial effect of the present invention:
1. providing multiple methods for taking out samples, and being applicable to most surgery occasions;
2. effectively preventing air leakage by providing multiple sealing structures;
3. quick discharge, which saves the surgery time; and
4. better fixing the puncture outfit, and preventing the trocar from loosening in surgery, which is convenient for medical workers to operate.

BRIEF DESCRIPTION OF THE DRAWINGS

The present invention is further described hereinafter with reference to the drawings and the embodiments.

FIG. 11-b is a structural diagram of an embodiment of a colored catheter sleeve according to the present invention; and FIG. 11-c is a diagram of combination of the puncturing tool and the colored catheter sleeve.

DETAILED DESCRIPTION

Figure 1:
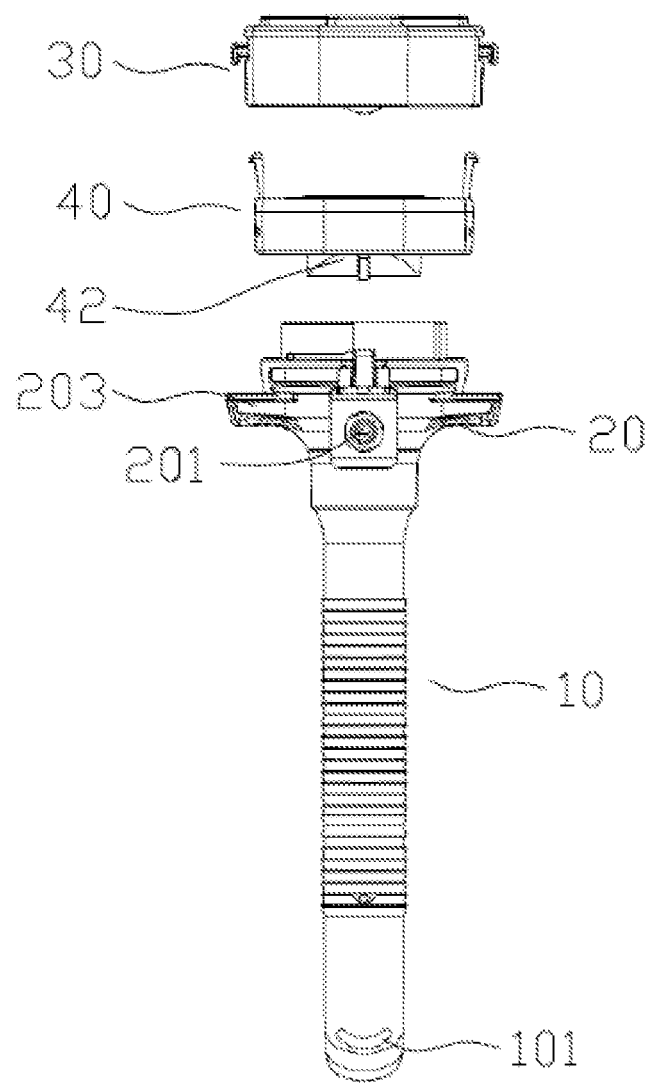
FIG. 1 is an exploded diagram of an embodiment of the present invention.

The concept, specific structure and generated technical effects of the present invention will be described clearly and completely hereinafter with reference to the embodiments and the drawings to fully understand the objects, solutions and effects of the present invention. It should be noted that the embodiments in the application and the features in the embodiments may be combined with each other in case of no conflict.

It should be noted that, unless otherwise specified, when a feature is referred to as "fixed" and "connected" to another feature, it can be fixed, connected to another feature directly or indirectly. In addition, the description of upper, lower, left, right and the like used in the present invention is only relative to the mutual positional relationship of the respective components of the present invention in the drawings.

In addition, unless otherwise defined, all the technical and scientific terms used herein are to be understood by those skilled in the art in general meaning. The terms used herein are for the purpose of describing particular embodiments only and are not intended to limit the present invention. The term "and/or" used in the text comprises any combination of one or more of the associated listed items.

Figure 2:
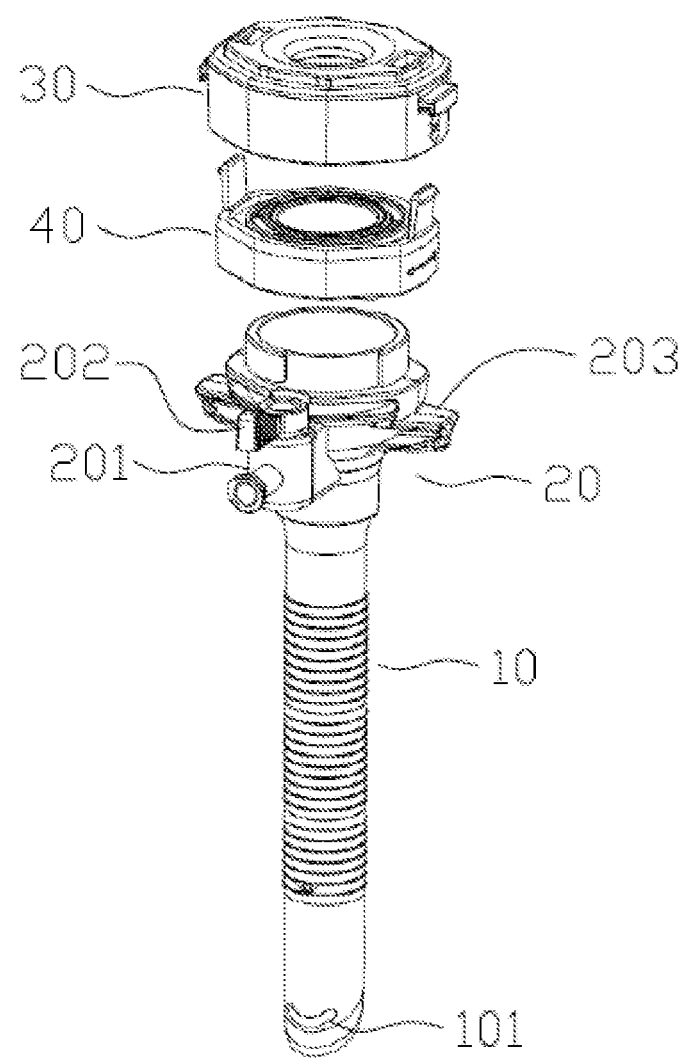
FIG. 2 is a stereoscopic diagram of FIG. 1.

Referring to FIG. 1 and FIG. 2, a trocar of the present invention comprises a catheter 10, a support 20 connected to one end of the catheter, and a channel running though the catheter and the support along an axial direction. Surgery instruments such as puncturing tool or endoscope can enter the enterocoelia along the channel to directly reach to a nidus, which prevents accidental injury.

In order to better realize the overall sealing, a primary sealing component 30 and a second sealing component 40 are arranged. The primary sealing component 30, the second sealing component 40 and the support 20 are connected together in a sealing manner from top to bottom in sequence, and can be independently detachable, so as to provide multiple methods for taking out tissues.

Figure 3:
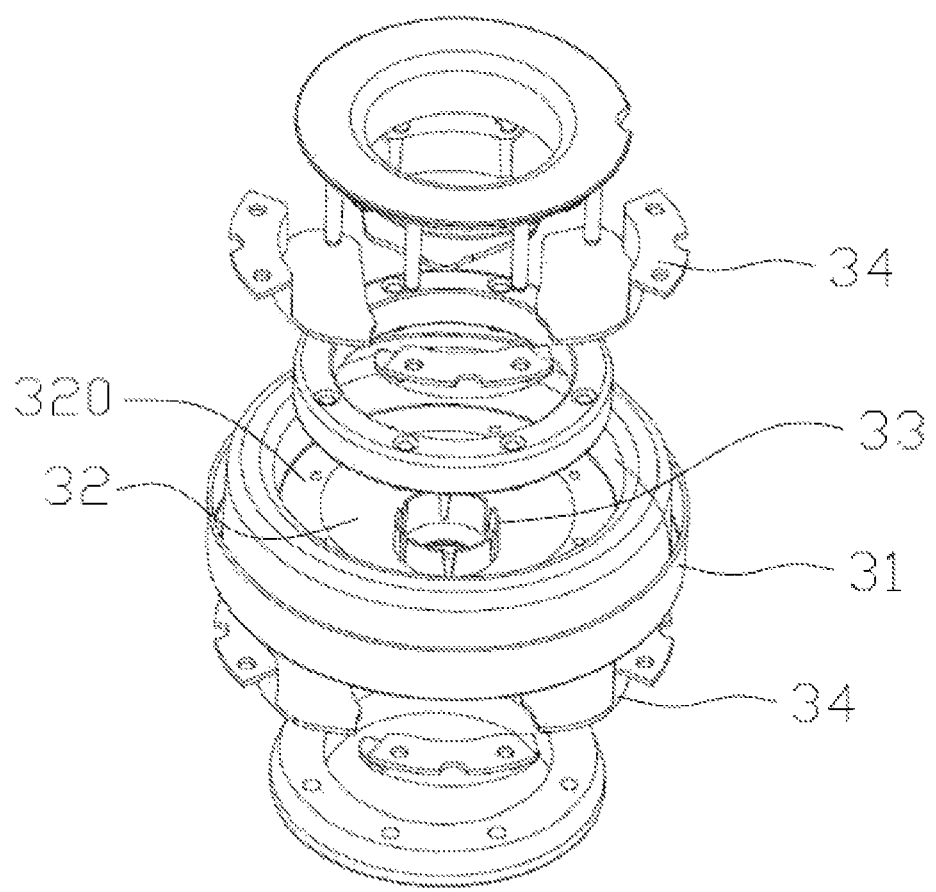
FIG. 3 is an exploded diagram of the internal structure of a first sealing component according to the present invention.

The primary sealing component 30 is used for sealing when a device is used. Referring to FIG. 3, the primary sealing component 30 preferably comprises a primary sealing seat 31 and a primary sealing membrane 32, the primary sealing seat 31 is provided with an axial through hole, the primary sealing membrane 32 is fixedly connected at an external edge 320 thereof to the through hole and has a center opened with a round hole 321. A device can be encircled by the primary sealing membrane 32 when passing through the round hole to form an airtight structure.

Since the primary sealing membrane 32 has elasticity, and the external edge thereof is fixed on the primary sealing seat 31, the primary sealing membrane 32 can be deformed to a certain extent during twisting of the device, so as to enable the round hole 321 to be fitted with the periphery of the surgery device all the time to guarantee the air impermeability. After the device is pulled out, the primary sealing membrane 32 can be recovered under an elastic effect.

Figure 4:
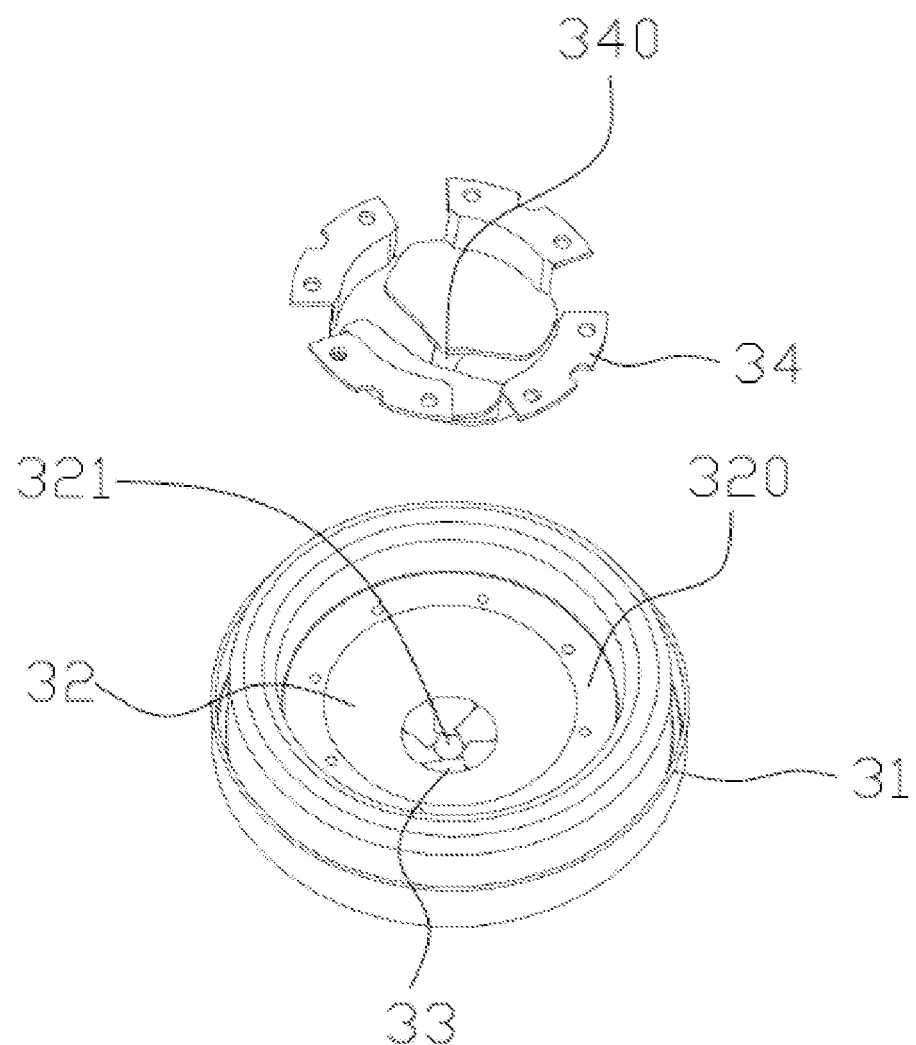
FIG. 4 is a structural diagram of a first sealing membrane and guide plates.

Moreover, in order to reach corresponding sealing effect, the round hole in the prior art is generally relatively small, so that it is very difficult to insert the surgery device, and it will cause air leakage if an smaller device is inserted because of the low recovering speed of the round hole. In order to overcome the defect, a plurality of sealing plates 33 is arranged. Referring to FIG. 4, the sealing plates 33 are uniformly arranged along the periphery of the round hole. Each sealing plate 33 has one end fixedly connected to the first sealing membrane 32, and the other end extending to the central region of the round hole 321, and the neighboring sealing plates 33 are partially overlapped to form a lens-type leaf structure. When a device passes through the round hole 321, the sealing plates are brought to move axially along the through hole and overlaps with each other while being fitted with the periphery of the device to form an airtight structure. The sealing plates can recover to an initial status quickly after the device is pulled out, so as to adapt to the sealing requirements of device with different sizes.

The primary sealing membrane 32 is provided with the sealing plates 33 at either side thereof, so as to enable the device to be encircled by the sealing plates 33 when the device is inserted and pulled out.

Preferably, in order to prevent the inserted device from deviating from the round hole to penetrate the primary sealing membrane 32, the primary sealing membrane 32 is provided with a plurality of guide plates 34 at either side thereof. Referring to FIG. 3 and FIG. 4, four guide plates 34 are preferable, and are mutually stacked to form a via hole 340 coaxial with the round hole 321. The surgery device, when inserted, is firstly guided by the via hole 340, and enters the round hole 321 under the guide of the guide plates 34 arranged around so as to prevent the device from deviating from the position to penetrate the primary sealing membrane, which causes air leakage.

Figure 5:
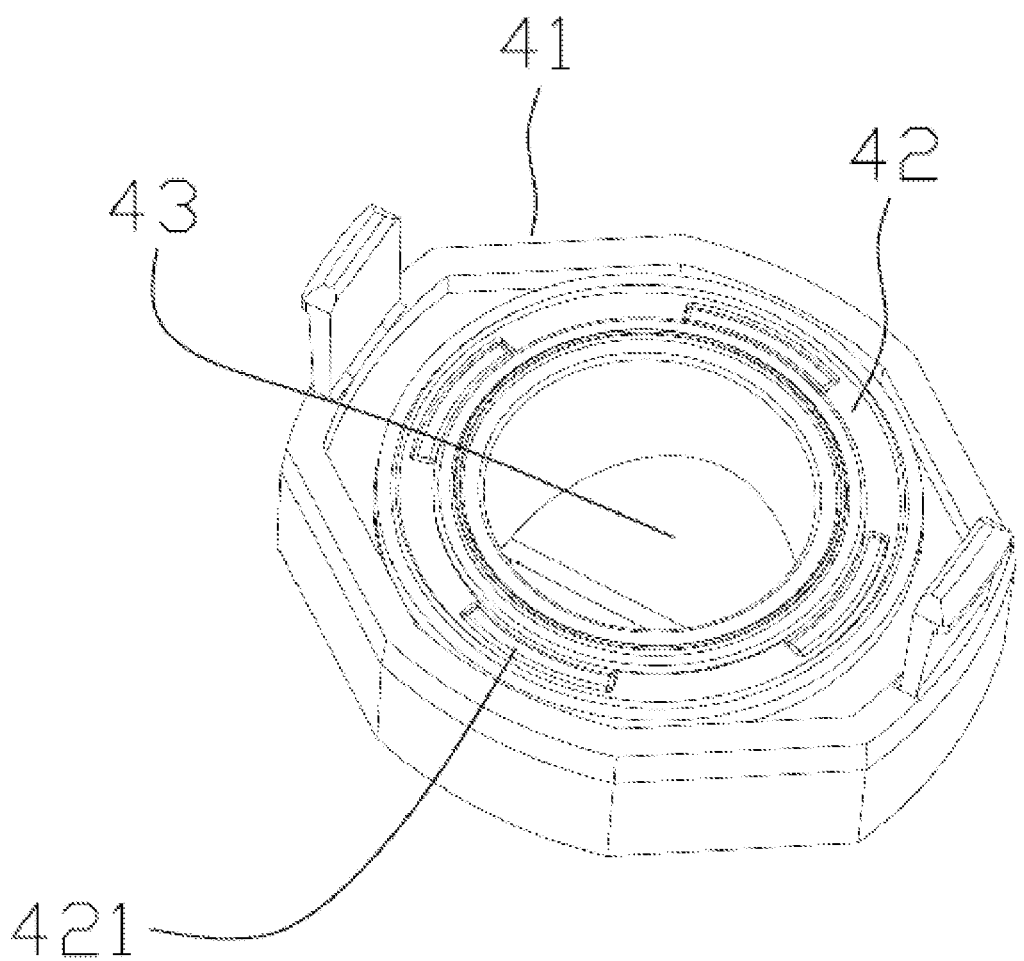
FIG. 5 is a stereoscopic diagram of an embodiment of a second sealing component.
Figure 6:
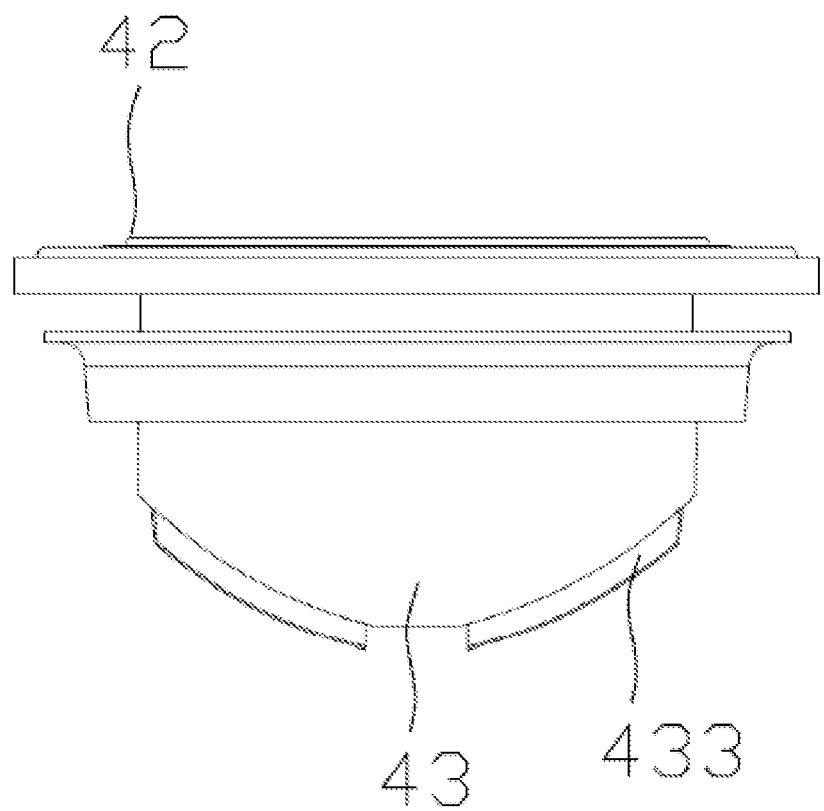
FIG. 6 is a side view of an embodiment of a second sealing membrane.
Figure 7:
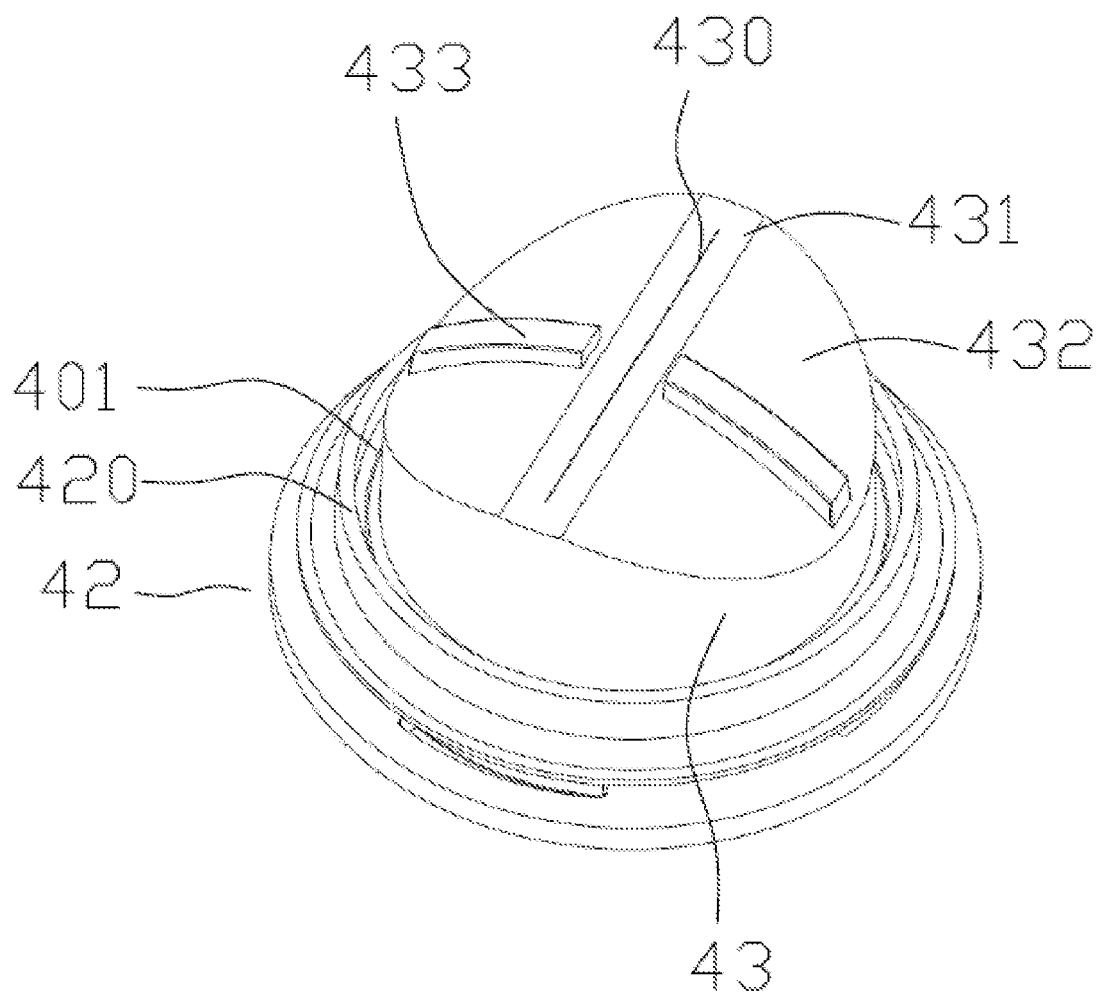
FIG. 7 is a stereoscopic diagram of FIG. 7.

The second sealing component 40 is used for sealing when no instrument is used. Referring to FIG. 5 to FIG. 7, the second sealing component 40 comprises a shell 41, a second sealing seat 42 and a second sealing membrane 43, wherein the second sealing seat 42 is provided with an axial through hole and connected to the shell 41 in a sealing manner, so as to enable the air to enter and exist through the through hole only.

The second sealing membrane 43 is fixedly connected at an outer edge thereof to the through hole and has a center provided with a finedraw 430. The finedraw 430 is locked by the second sealing membrane 43 itself depending on the elastic force thereof when there is no device passing through and is opened under an external force when the second sealing membrane 43 is squeezed by a surgery device, to enable the second sealing membrane to be naturally closed to form an airtight structure without hindering the normal insertion of the device.

The second sealing seat 42 is provided with a sealing structure for connecting to the shell in a sealing manner, and preferably, the sealing structure is a sealing ring 420 arranged along the periphery of the through hole. When connecting the second sealing seat 42 to the shell 41, in order to prevent the sealing ring 420 from driving the deformation of the second sealing membrane 43, referring to FIG. 7 and FIG. 10, a gap 401 is arranged between the second sealing membrane 43 and the sealing ring 420 to separate the second sealing membrane 43 and the sealing ring 420.

The second sealing seat 42 is fixedly connected to the shell 41, and the movement thereof relative to the shell 41 is limited to avoid the deformation of the sealing ring 420 under the friction force, which affects the sealing effect. Specifically, the second sealing seat 42 is uniformly provided with a plurality of fixing holes 421, the shell 41 is provided with fixing posts (not shown) corresponding to the fixing holes 421, and when the second sealing seat 42 is installed on the shell 41, the fixing columns are inserted into the fixing holes to lock the second sealing seat.

The second sealing membrane 43 comprises a plane 431 provided with the finedraw 430, and cambered surfaces 432 arranged at either side of the plane, and the cambered surfaces 432 form a spherical surface structure that can bear double enterocoelia pressure without air leakage and provide an elastic force to the second sealing membrane 43 to lock the finedraw 430.

The camber surface 432 is provided with a reinforcing rib 433 perpendicular to the finedraw 430, which can further strengthen the locking force to the finedraw 430, so as to enable the finedraw 430 to be recovered to the airtight state quickly after the device is pulled out.

A good sealing effect can be realized no matter there is a surgery device or not with combination of the primary sealing component 30 and the second sealing component 40.

In the embodiment, the primary sealing component 30 is clamped to the second sealing component 40 which is in turn clamped to the support 20. The first sealing component 30, the second sealing component 40 and the support 20 can be separated by operating a clamping part, thus forming three methods for taking out objects: if the volume of a tissue is normal, the tissue can be directly taken out by a normal method; if the tissue is relatively large, the primary sealing component 30 can be firstly disassembled, and the relatively large tissue can pass through the second sealing membrane 43 because of a relatively large degree of deformation caused by the finedraw 430; if the deformation degree of the second sealing membrane 43 is insufficient to take out the tissue, the primary sealing component 30 and the second sealing component 40 can be disassembled at the same time and taken out through the support. Meanwhile, the air may be discharged through the opening of the support and the air-inflated structure when needed, which accelerates the air discharge, and saves the surgery time.

Figure 8:
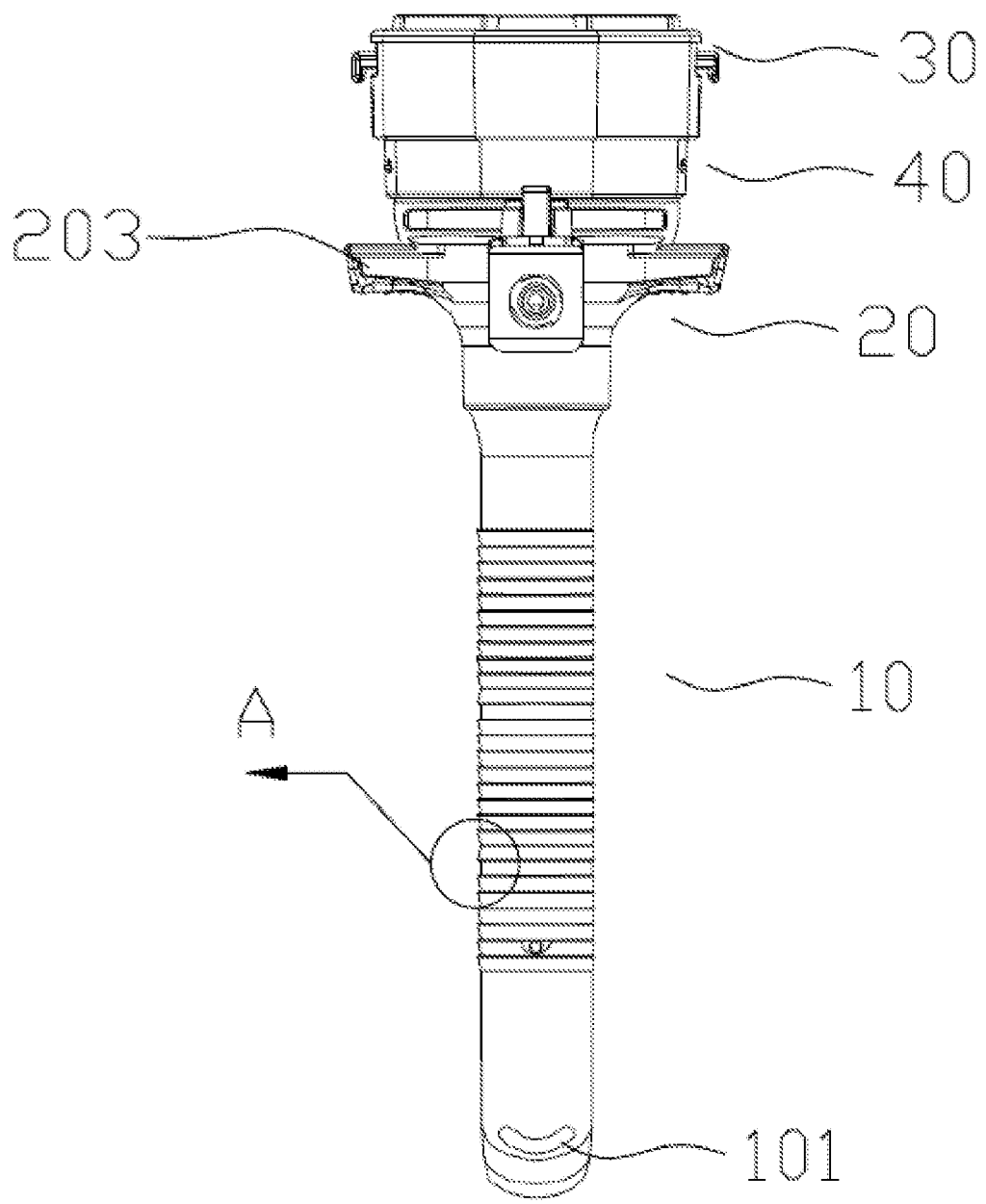
FIG. 8 is a side view of an embodiment of the present invention.
Figure 9:
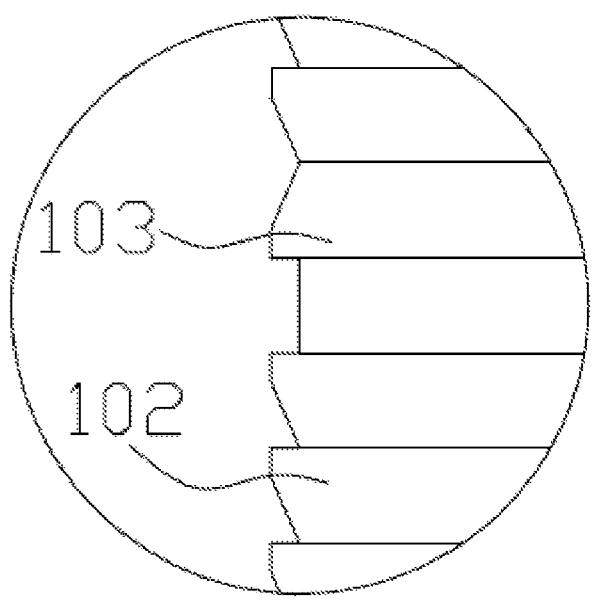
FIG. 9 is a partial diagram along a direction A in FIG. 8.

Referring to FIG. 8 and FIG. 9, the catheter 10 is uniformly provided with a plurality of first barbs 102 at an outer surface thereof, which can increase the friction force when pulling the cannula 10. Preferably, a plurality of second barbs 103 are arranged among the first barbs and spaced apart a certain distance from one another. The first barbs 102 are oriented opposite to the second barbs 103. Compared to the prior art in which only unidirectional barbs are arranged, the surface layer tissue of enterocoelia can be clamped between the first barb 102 and the second barb 103, so as to further strengthen the stability of the cannula.

Referring to FIG. 8, in order to facilitate the observation to the movement condition of the internal punctured object, the cannula 10 is generally made of transparent material, and the condition that the cannula 10 is inserted too deep due to the invisibility of the position of the cannula 10 is possible to occur in the actual use. In the embodiment, the cannula 10 is provided at an end thereof with an indication structure, which is preferably a black radiography line 101, and the pass-through condition of the transparent cannula 10 in the abdomen can be observed through the black radiography line 101, so as to avoid the above situation.

The support 20 is provided with an annular kinking structure 203, during the surgery, a suture can pass through the kinking structure 203 and fixed to the skin, so as to enable the cannula 10 not to be affected by the operation of pulling out the surgery device.

Figure 10:
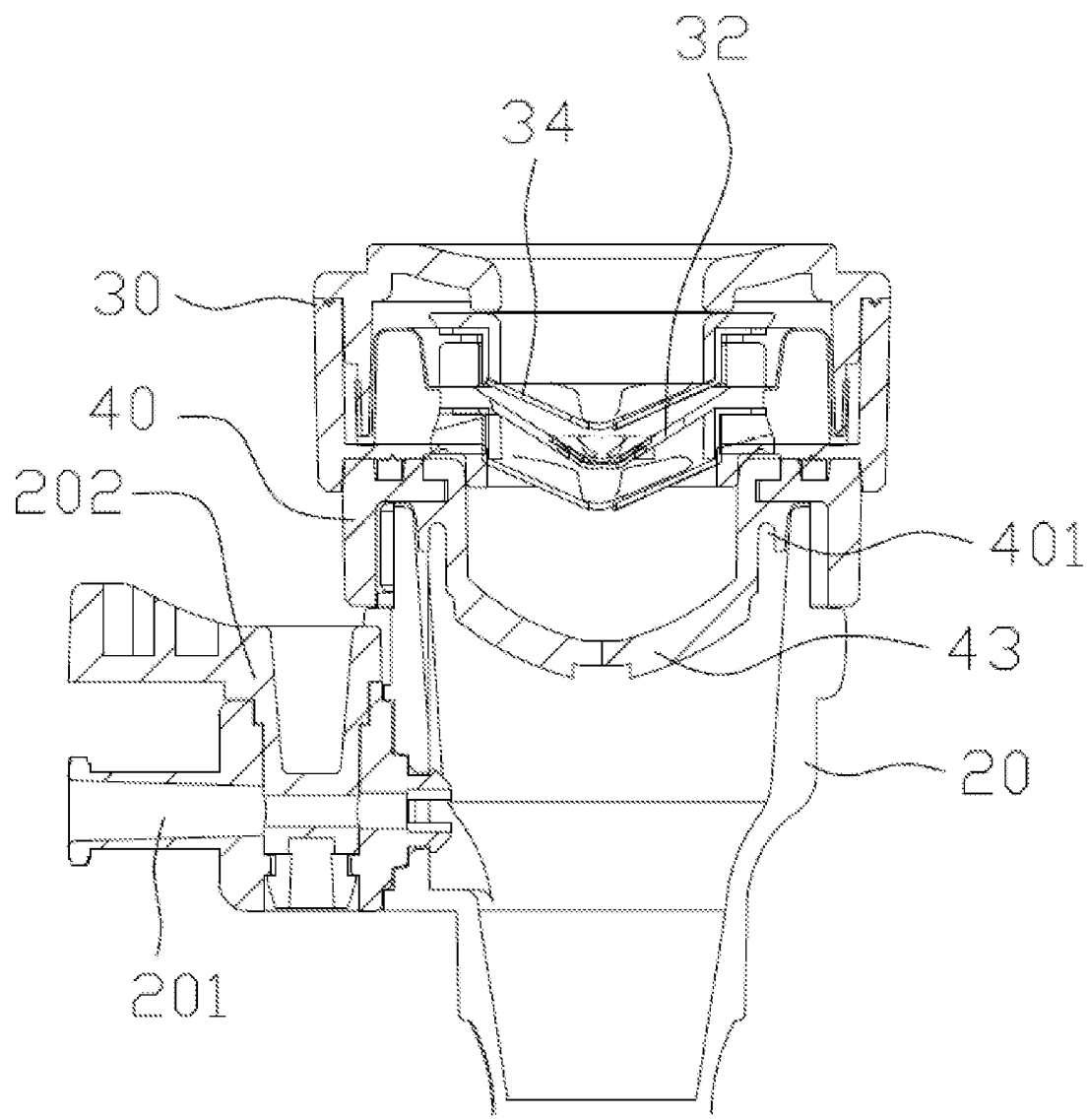
FIG. 10 is a cross-section diagram of combination of the first sealing component, the second sealing component and the support according to the present invention.

Referring to FIG. 10, the support 20 is provided with an air-inflated structure 201 communicated with the channel, the air can be injected into the enterocoelia through the air-inflated structure, and similarly, the air can be also discharged through the air-inflated structure. The air-inflated structure 201 is provided with an air valve 202 for controlling on-off of the air-inflated structure 201.

The air-inflated structure 201 in the prior art generally utilizes UV glue for the purpose of solidification and sealing, this bonding process has the disadvantages of low connecting strength and being easy to lose efficacy because of ageing. In order to solve this problem, according to the present invention, the air-inflated structure 201 is fixed to the support 20 through a snap-fit connection firstly, and then the solidification of the air-inflated structure is separated from the sealing through the method of sealing by UV glue. Compared to the single glue joint form, the fixing strength of the air-inflated structure 201 can be increased to prevent the phenomenon of air leakage caused by collision and other damages of external force.

The first sealing membrane 32 is of a funnel shape, and protrudes towards the cannula, so as to facilitate the insertion of the surgery device.

Figure 11:
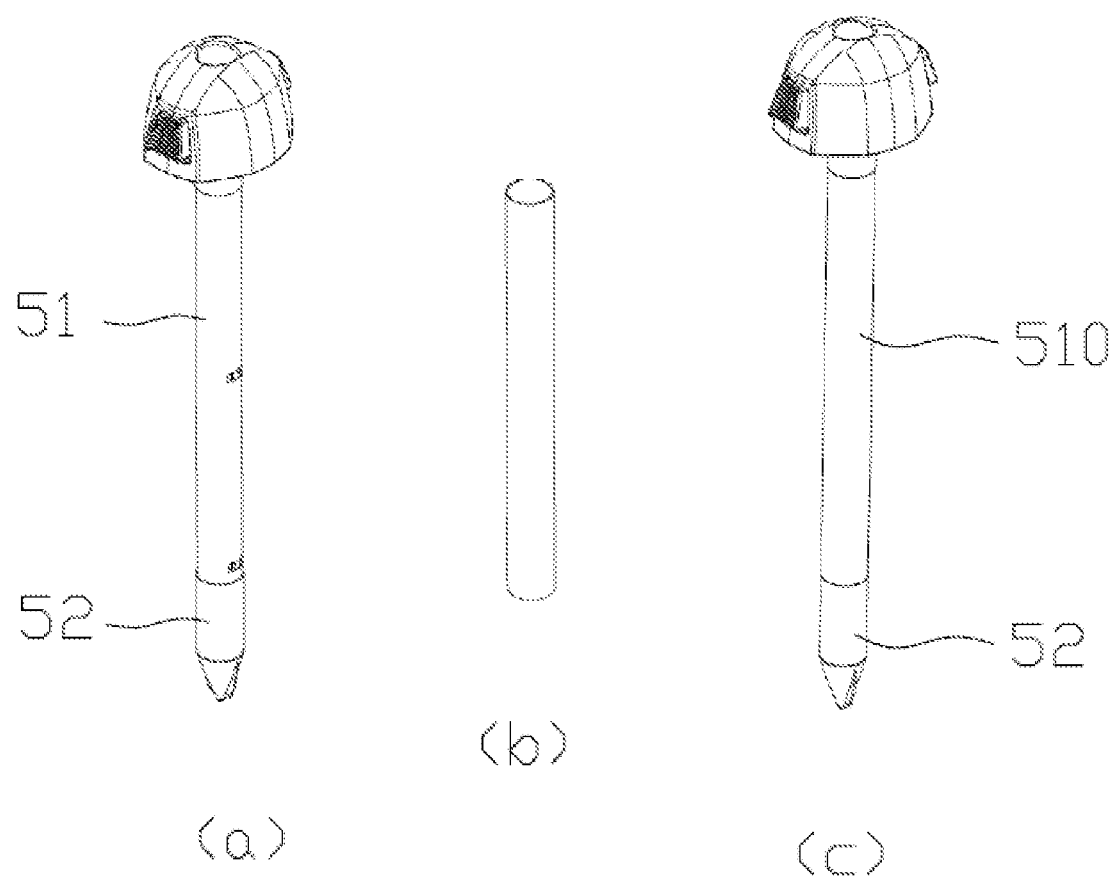
FIG. 11-a is a structural diagram of an embodiment of a puncturing tool according to the present invention.

According to the present invention, further comprising a puncturing tool cooperative with the trocar. Referring to FIG. 11-a, the puncturing tool comprises a toolbar 51 and a tool bit 52. Distinguished from the method that the visual tool bit is adhered to the stainless steel toolbar in the prior art, the toolbar 51 and the tool bit 52 are formed by an integral molding technique, which can effectively prevent the tool bit from being broken. Referring to FIG. 11-b and FIG. 11-c, the toolbar 51 is covered with a colored catheter sleeve 510, which can facilitate the medical workers to observe whether the toolbar penetrates an abdominal wall.

The contents above specifically describe the preferred embodiments of the present invention, but the present invention is not limited to the embodiments, those skilled in the art may make various equivalent changes or replacements without departing from the spirit of the present invention, and these equivalent changes or replacements shall all fall within the scope limited by the claims of the application.

What is claimed is:

1. A fully detachable trocar, comprising:
   a cannula;
   a support connected to one end of the cannula;
   a channel passing through the cannula and the support along an axial direction;
   an air-inflated structure arranged on the support and communicated with the channel;
   an air valve for controlling the air-inflated structure to turn on and off;
   a primary sealing component for sealing when a device is used; and
   a second sealing component for sealing when no device is used;
   said primary sealing component, said second sealing component and said support being connected in a sealing manner from top to bottom in sequence;
   said primary sealing component being independently separated from said second sealing component;
   said second sealing component being independently separated from said support;
   said second sealing component including,
      a shell,
      a second sealing seat arranged within and connected to the shell in a sealing manner, the second sealing seat is provided with an axial through hole, and
      a second sealing membrane fixedly connected at an outer edge thereof to the through hole and provided at a center thereof with a finedraw so that said primary sealing membrane can be naturally closed to form an airtight structure when no device is used, and normal insertion of the device cannot be hindered either;
   said second sealing seat being provided with a sealing structure for sealing with said shell;
   said second sealing membrane and the sealing structure being mutually separated so that said second sealing membrane cannot be deformed due to said sealing connection between said second sealing seat and said shell;
   said second sealing seat being fixedly connected to said shell so as to limit the movement thereof relative to said shell and avoid said sealing structure from deformation under a friction force;
   said second sealing membrane including a plane provided with the finedraw and cambered surfaces arranged at either side of the plane;
   each of said cambered surfaces being provided with a reinforcing rib perpendicular to the finedraw which enables the finedraw to be recovered quickly after the device is pulled out, so as to avoid air leakage.

2. The fully detachable trocar according to claim 1, wherein the primary sealing component comprises:
   a primary sealing seat with an axial through hole;
   a primary sealing membrane fixedly connected at an external edge thereof to the through hole and provided at a center thereof with a round hole, wherein the device can be encircled by the primary sealing membrane when passing through the round hole to form an airtight structure, and a close-fitting with the device can be maintained by the first sealing membrane as the device moves;
   a plurality of sealing plates uniformly arranged along a periphery of the round hole, with one end being fixedly connected to the primary sealing membrane and the other end extending to a central region of the round hole, wherein neighboring sealing plates are partially overlapped to form a lens-type leaf structure;
   when the device passes through the round hole, the sealing plates are fit with a periphery of the device to form an airtight structure, and can recover to an initial status quickly after the device is pulled out, so as to adapt to the sealing requirements of instruments with different sizes; and the sealing plates are arranged at either side of the round hole to enable the instrument to keep sealing in the process of inserting in and pulling out.

3. The fully detachable trocar according to claim 2, wherein the primary sealing component comprises a plurality of guide plates, the guide plates collectively form a via hole coaxial with the round hole for guiding the instrument so that the device can only pass through the round hole, which prevents the device from deviation to puncture the first sealing membrane to cause air leakage; and wherein the guide plates are arranged at either side of the primary sealing membrane.

4. The fully detachable trocar according to claim 1, wherein the cannula comprises:
  a plurality of first barbs uniformly arranged at an outer surface of the catheter; and
  a plurality of reversed second barbs arranged among the first barbs and spaced apart a certain distance from one another;
the first barbs and the second barbs are used for fixing the cannula in two directions, and preventing the device when pulled out from driving the cannula to divorce from a human body.

5. The fully detachable trocar according to claim 4, wherein the cannula has an end with an indication structure to facilitate displaying a position of the cannula.

6. The fully detachable trocar according to claim 5, wherein the support is provided with an annular kinking structure, which can fix the cannula onto skin through suture.

7. The fully detachable trocar according to claim 6, wherein the air-inflated structure is clamped in the support and is sealed by glue.

8. The fully detachable trocar according to claim 1, further comprising a puncturing tool including a toolbar with a colored cannula sleeve and a tool bit integratedly connected to the toolbar.

* * * * *